(12) United States Patent
Tsao et al.

(10) Patent No.: US 9,283,043 B2
(45) Date of Patent: Mar. 15, 2016

(54) APPARATUS, SYSTEM, AND METHOD FOR ROBOTIC MICROSURGERY

(75) Inventors: Tsu-Chin Tsao, Manhattan Beach, CA (US); Steven D. Schwartz, Los Angeles, CA (US); Jean-Pierre Hubschman, Beverly Hills, CA (US); Jason T. Wilson, Los Angeles, CA (US); Stephen W. Prince, Los Angeles, CA (US); Jean-Louis Bourges, Paris (FR)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 752 days.

(21) Appl. No.: 13/522,313
(22) PCT Filed: Jan. 14, 2011
(86) PCT No.: PCT/US2011/021405
§ 371 (c)(1), (2), (4) Date: Jan. 7, 2013
(87) PCT Pub. No.: WO2011/088400
PCT Pub. Date: Jul. 21, 2011

(65) Prior Publication Data
US 2013/0123798 A1    May 16, 2013

Related U.S. Application Data

(60) Provisional application No. 61/295,153, filed on Jan. 14, 2010.

(51) Int. Cl.
*A61B 19/00* (2006.01)
(52) U.S. Cl.
CPC ............... *A61B 19/20* (2013.01); *A61B 19/201* (2013.01); *A61B 19/22* (2013.01); *A61B 19/50* (2013.01)
(58) Field of Classification Search
CPC .... A61B 19/201; A61B 19/20; A61B 19/203; A61B 19/22; A61B 19/50; A61B 2019/5287; A61B 19/5244; A61B 19/2203

USPC .......................................... 606/107, 129, 130
See application file for complete search history.

(56) References Cited

U.S. PATENT DOCUMENTS 3,910,535 A   10/1975   Ohnaka
4,899,730 A    2/1990   Stennert et al.
(Continued)

FOREIGN PATENT DOCUMENTS

EP         1 681 029 A1   7/2006
WO       WO-96/39944    12/1996
(Continued)

OTHER PUBLICATIONS

PCT/US2011/021405, Int'l Search Report dated Sep. 21, 2011.
(Continued)

*Primary Examiner* — Katherine M Shi
(74) *Attorney, Agent, or Firm* — Foley & Lardner LLP; Cliff Z. Liu

(57) ABSTRACT

A system for microsurgery includes a first assembly and a second assembly, each including: (1) a planar remote center of motion (RCM) device configured to constrain motion of a surgical instrument attached to the planar RCM device such that an axis of the surgical instrument passes through the RCM while remaining in a planar region defined based on a rotational orientation of the planar RCM device; and (2) a rotational device attached to the planar RCM device and configured such that an axis of rotation of the rotational device passes through the remote center of motion. The rotational orientation of the planar RCM device is defined about the axis of rotation. The first assembly and the second assembly are configured to be positioned such that a distance between the remote centers of motion of the first assembly and the second assembly is no greater than two centimeters.

7 Claims, 16 Drawing Sheets

(56) References Cited

U.S. PATENT DOCUMENTS

| | | | |
|---|---|---|---|
| 5,053,687 | A | 10/1991 | Merlet |
| 5,086,401 | A | 2/1992 | Glassman et al. |
| 5,330,485 | A | 7/1994 | Clayman et al. |
| 5,410,638 | A | 4/1995 | Colgate et al. |
| 5,697,939 | A * | 12/1997 | Kubota et al. ............ 606/130 |
| 5,824,007 | A * | 10/1998 | Faraz et al. ............ 606/130 |
| 6,264,665 | B1 | 7/2001 | Yu et al. |
| 6,406,472 | B1 | 6/2002 | Jensen |
| 6,413,263 | B1 * | 7/2002 | Lobdill et al. ............ 606/129 |
| 6,477,912 | B2 | 11/2002 | Song et al. |
| 6,620,174 | B2 | 9/2003 | Jensen et al. |
| 2004/0220588 | A1 * | 11/2004 | Kermode et al. ............ 606/129 |
| 2007/0151389 | A1 | 7/2007 | Prisco |
| 2008/0111513 | A1 | 5/2008 | Farritor et al. |
| 2009/0012534 | A1 | 1/2009 | Madhani et al. |
| 2009/0271035 | A1 | 10/2009 | Lurz et al. |
| 2013/0296886 | A1 | 11/2013 | Green et al. |

FOREIGN PATENT DOCUMENTS

| | | |
|---|---|---|
| WO | WO 2007/147232 A1 | 12/2007 |
| WO | WO 2008/123855 A1 | 10/2008 |
| WO | WO-2008/134017 | 11/2008 |
| WO | WO-2009/072535 | 6/2009 |
| WO | WO 2009/128958 A1 | 10/2009 |
| WO | WO-2009/140688 | 11/2009 |

OTHER PUBLICATIONS

EP Search Report from EP 11733487.0 dated Jan. 31, 2014.
International Search Report from PCT/US2011/021405 dated Sep. 21, 2011.
Douglas R.S., "Robotic Surgery in Ophthalmology: Reality or Fantasy?" Br. J. Ophthalmol., (2007), 91(1), p. 1.
Guerrouad et al., Advantage of Computer Aided Teleoperation (C.A.T.) in Microsurgery, IEEE Conference Proceeding, (1991) 1, pp. 910-914.
Guerrouad et al., "Automatic Analysis of Weariness During a Micromanipulation Task by MOS," IEEE Conference Proceeding, (1989), 3, pp. 906-907.
Guerrouad et al., "S.M.O.S.: Stereotaxical Microtelemanipulator for Ocular Surgery," IEEE Conference Proceeding, (1989), 3, pp. 879-880.
Hayat et al., "Conception of Information Tools to Assist the Surgeon When He Carries Out Radial Keratotomy With a Microtelemanipulator," IEEE Conference Proceeding, (1995), pp. 3.5-3.6.
Mines et al., "Feasibility of Telerobotic Microsurgical Repair of Corneal Lacerations in an Animal Eye Model," J. Telemed. Telecare, (2007), 13(2), pp. 95-99.
Panait et al., "Applications of Robotic Surgery," Chiruria (Buc.), (2002), 97(6), pp. 549-555.
Pournaras et al., "New Ocular Micromanipulator for Measurements of Retinal and Vitreous Physiologic Parameters in the Mammalian Eye," Exp. Eye Res., (1991), 53, pp. 723-727.
Taylor et al., "A Steady-Hand Robotic System for Microsurgical Augmentation," The International Journal of Robotics, (1999), 18, pp. 1201-1210.
Tsirbas et al., "Robotic Ocular Surgery," Br. J. Ophthalmol., (2007), 91(1), pp. 18-21.
Yu et al., "Robotic Ocular Ultramicrosurgery," Aust N.Z. J. Ophthalmol, (1998), 26; Suppl. 1, pp. S6-S8.

* cited by examiner

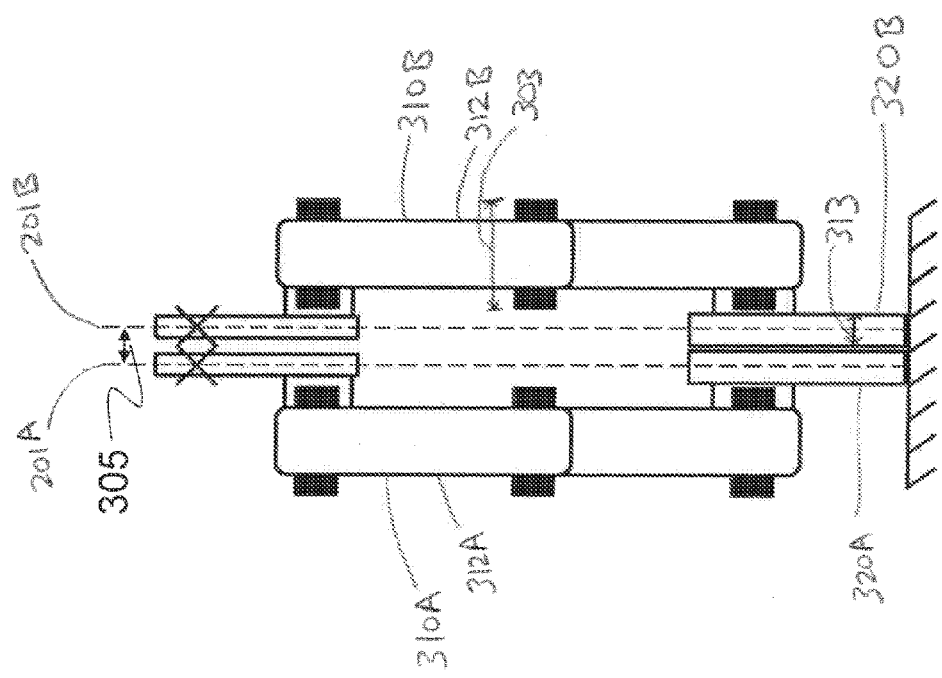

APPARATUS, SYSTEM, AND METHOD FOR ROBOTIC MICROSURGERY

CROSS-REFERENCE TO RELATED APPLICATION

The present application is a 35 USC 371 National Stage Entry of PCT/US2011/021405 filed Jan. 14, 2011, which claims the benefit of U.S. Provisional Application No. 61/295,153 filed Jan. 14, 2010, the disclosure of which are incorporated hereby by reference in their entirety.

FIELD OF THE INVENTION

The invention relates generally to the field of microsurgery. More particularly, the invention relates to minimally invasive robotic microsurgery.

BACKGROUND

Minimally invasive surgery has benefited from a shift to robotic procedures rather than standard instrument in hand techniques. Specifically, laparoscopic procedures such as general surgery, urology, cardiovascular surgery and gynecology have benefited from teleoperated robotic surgery providing increased safety and faster recovery time. However, standard laparoscopic devices are typically not suitable for minimally invasive microsurgery. In particular, the bulkiness of previous robotic designs generally prevents the positioning of two or more surgical instruments with remote centers of motion in close proximity for microsurgery.

It is against this background that a need arose to develop the apparatus, system, and method for robotic microsurgery described herein.

SUMMARY

One aspect of the invention relates to a system for microsurgery. In one embodiment, the system comprises a first assembly and a second assembly, each including: (1) a planar remote center of motion device configured to constrain motion of a surgical instrument attached to the planar remote center of motion device such that an axis of the surgical instrument passes through a remote center of motion while remaining in a planar region defined based on a rotational orientation of the planar remote center of motion device; and (2) a rotational device attached to the planar remote center of motion device and configured such that an axis of rotation of the rotational device passes through the remote center of motion, where the rotational orientation of the planar remote center of motion device is defined about the axis of rotation. The first assembly and the second assembly are configured to be positioned such that a distance between the remote center of motion of the first assembly and the remote center of motion of the second assembly is no greater than two centimeters.

Another aspect of the invention relates to a method of controlling motion of surgical instruments. In one embodiment, the method comprises: (1) positioning a first device and a second device such that a first remote center of motion associated with the first device and a second remote center of motion associated with the second device are maintained as spatially separate and in close proximity for microsurgery; (2) attaching a first surgical instrument to the first device, where the first device constrains motion of the first surgical instrument such that an axis of the first surgical instrument passes through the first remote center of motion; (3) attaching a second surgical instrument to the second device, where the second device constrains motion of the second surgical instrument such that an axis of the second surgical instrument passes through the second remote center of motion; and (4) rotating the first device and the second device, while maintaining spatial separation between the first device and the second device and between the first surgical instrument and the second surgical instrument based on a first rotational orientation of the first device and a second rotational orientation of the second device.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of some embodiments of the invention, reference should be made to the following detailed description taken in conjunction with the accompanying drawings.

FIG. 5 illustrates a top view of a first remote center of motion assembly positioned adjacent to a second remote center of motion assembly, where the two assemblies are in an offset configuration, according to an embodiment of the invention;

DETAILED DESCRIPTION

Definitions

The following definitions apply to some of the aspects described with respect to some embodiments of the invention. These definitions may likewise be expanded upon herein.

As used herein, the singular terms "a," "an," and "the" include plural referents unless the context clearly dictates otherwise. Thus, for example, reference to an object can include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

Description of Embodiments of the Invention

Figure 1:
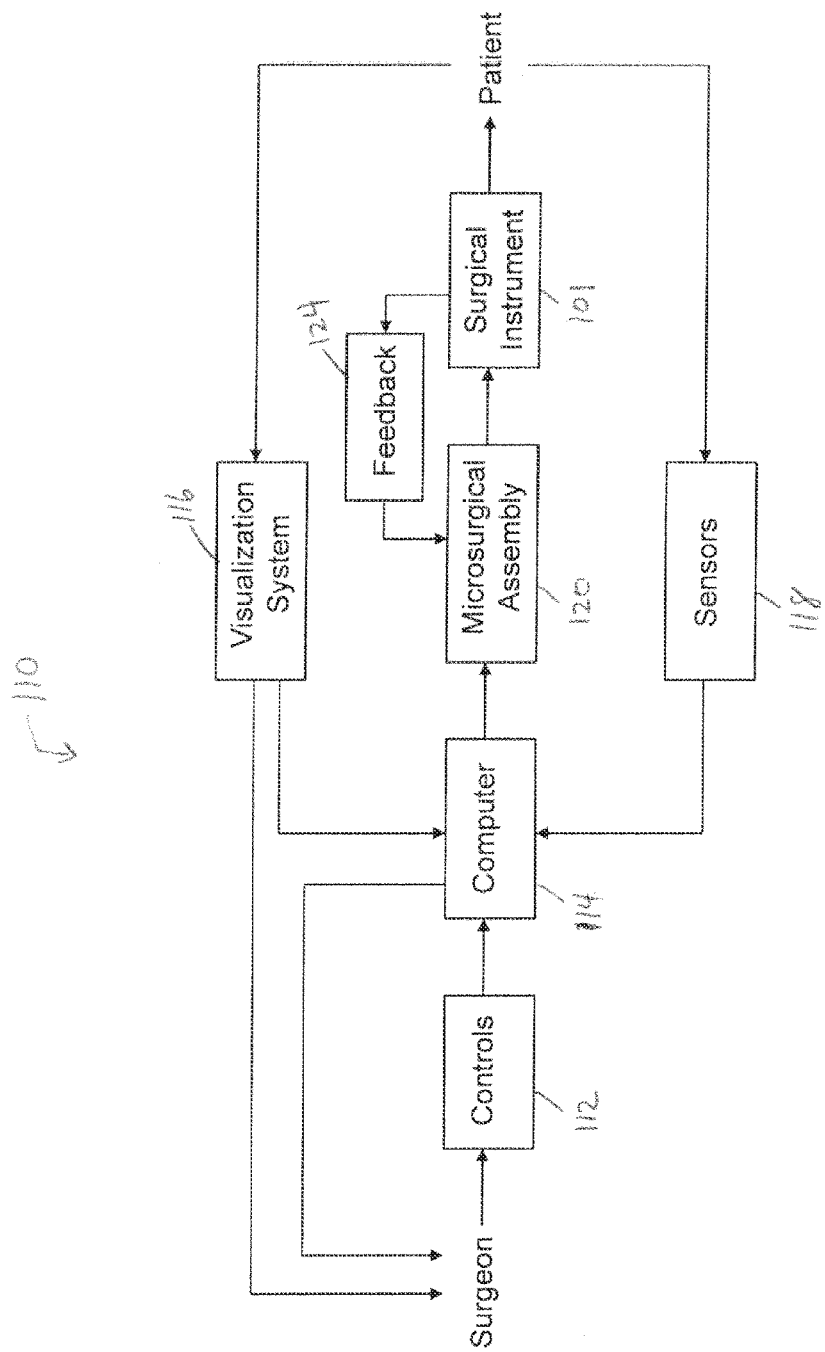
FIG. 1 illustrates a system for robotic microsurgery, according to an embodiment of the invention.

Attention first turns to FIG. 1, which illustrates a system 110 for robotic microsurgery, according to an embodiment of the invention. In the system 110, a surgeon manipulates controls 112. A computer 114 (further described with reference to FIG. 12) processes inputs received from the controls 112, a visualization system 116, and sensors 118. The visualization system 116 may perform imaging of a patient and/or the patient's environment. The sensors 118 may monitor the patient and/or the patient's environment. Based on processing by the computer 114, outputs are provided to a microsurgical assembly 120, and may also be provided to the surgeon. The surgeon may manipulate the controls 112 based on patient information provided by the visualization system 116 and/or outputs provided by the computer 114. For example, the surgeon may observe the surgery through the visualization system 116 and correspondingly manipulate the controls 112. The microsurgical assembly 120 is a mechanical assembly controlled by the computer 114. In one embodiment, the microsurgical assembly 120 selects surgical instruments 101 and applies the surgical instruments 101 to the patient in response to commands from the computer 114. The microsurgical assembly 120 may include a manipulator including robotic arms, each of which can translate, rotate, and otherwise manipulate one or more of the surgical instruments 101. The microsurgical assembly 120 may include feedback control loops 124 to stabilize motion of the surgical instruments 101, such as by rejecting undesirable external disturbances.

In one embodiment, the controls 112 may be part of a control console. The control console may house a visualization and control interface from the surgeon to interact with the microsurgical assembly 120 and the surgical site. The visualization and control interface may include a viewfinder allowing several views, e.g., global, angled, zoomed, intra-organ/endoscopic, and stereoscopic. There may be controls to switch between these views to allow the surgeon to visualize the surgical field appropriately.

The control console may also include two joysticks. By manipulating the two joysticks, the surgeon can operate the microsurgical assembly 120 to precisely manipulate the surgical instruments 101. For the surgeon to operate the microsurgical assembly 120 intuitively, the joysticks should provide the same degrees of freedom as the manipulators of the microsurgical assembly 120 that are being controlled by the joysticks. For external surgical procedures the joysticks can have six degrees of freedom, three translational and three rotational, to allow for independent control of all axes of motion. During internal surgical procedures, the joysticks can have at most four degrees of freedom, one translational and three rotational, to allow motions inside of the patient while enforcing a remote center of motion. In one embodiment, the joysticks can have fewer than four degrees of freedom, such as two degrees of freedom, one translational and one rotational, or three degrees of freedom, one translational and two rotational. Although the motions of the surgical instruments 101 may be scaled to provide higher accuracy than that achievable by the surgeon alone, the directions of the motions specified by the surgeon should be maintained by the microsurgical assembly 120. Also, the joysticks should be balanced in the sense that if the surgeon lets go of a joystick, the joystick stays in position. This prevents the manipulators, and hence the surgical instruments 101, from moving undesirably if the surgeon releases the joystick.

The manipulator of the microsurgical assembly 120 may have two or more robotic arms. If the manipulator has more than two arms, the control console may allow the surgeon to select the arms to be controlled by the surgeon, and to correspondingly switch the controls, including but not limited to the joysticks.

In one embodiment, the control console may include one or more foot pedals. The foot-pedals may control position of visualization devices, actuation of the devices used (including both the surgical instruments 101 and other devices), and/or the allowable degrees of freedom of the manipulators.

The visualization system 116 may include a camera that allows the surgeon to view the surgical field. The camera may convert an optical image of the surgical field into a digital signal that can be provided to the computer 114 for processing. The visualization system 116 may also include a microscope such as an ophthalmic microscope, an endoscope, and other visualization tools used for microsurgery. The visualization system is not limited to providing optical images of the patient. In one embodiment, the visualization system 116 may also include instruments corresponding to other imaging modalities, including but not limited to X-ray, CT, OCT, and MRI.

The sensors 118 include any sensors that monitor the patient or the patient's environment. For example, the sensors 118 may detect and measure motion by the patient. In one embodiment, such as for ophthalmic microsurgery, the sensors 118 may be associated with a head restraint (further described with reference to FIGS. 11 and 12).

The surgical instruments 101 are tools for using and/or manipulating tissues, drugs, fluids, light or other energy beams, data, and solid bodies (such as a needle or a foreign body) during a surgical procedure. The surgical instruments 101 may include but are not limited to forceps, scissors, cauterizers, manipulators, choppers, hooks, cannula such as infusion cannula, calipers, clamps, lens, needles, needle holders, blades, spatulas, syringes, vitreous cutters, endoscopes, light sources including but not limited to light probes and laser probes, sensors, and cameras.

Figure 2:
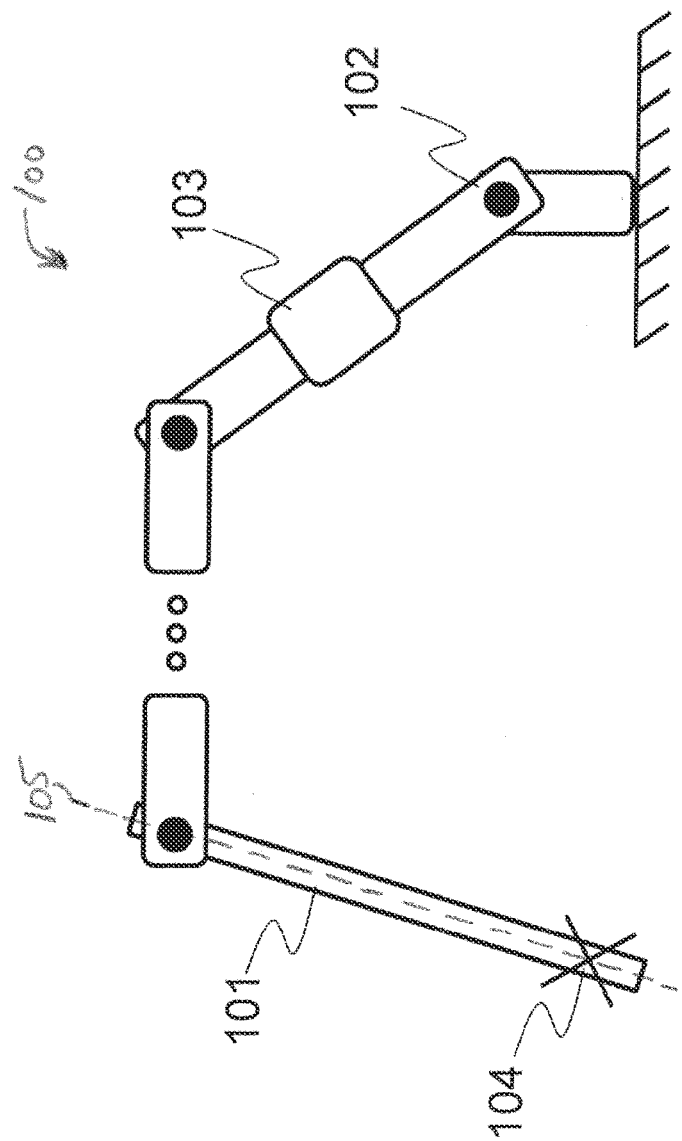
FIG. 2 illustrates a planar remote center of motion device, according to an embodiment of the invention.

The microsurgical assembly 120 is further described with reference to FIG. 2 through FIG. 10. FIG. 2 illustrates a planar remote center of motion device 100, according to an embodiment of the invention. The microsurgical assembly 120 (see FIG. 1) may include a planar remote center of motion device 100 that may hold and/or otherwise be attached to the surgical instrument 101. The planar remote center of motion device 100 constrains motion of the surgical instrument 101 such that an axis 105 of the surgical instrument 101 remains in a planar region. In one embodiment, the planar remote center of motion device 100 constrains the surgical instrument 101 such that the axis 105 of the surgical instrument 101 cannot translate or rotate out of the planar region. The planar remote center of motion device 100 may include one or more rotational joints 102 and/or prismatic joints 103. These joints may be oriented in a serial fashion, a parallel fashion, or both. The planar remote center of motion device 100 is also configured such that the surgical instrument 101 passes through a point in space referred to as a remote center of motion 104.

Figure 3:
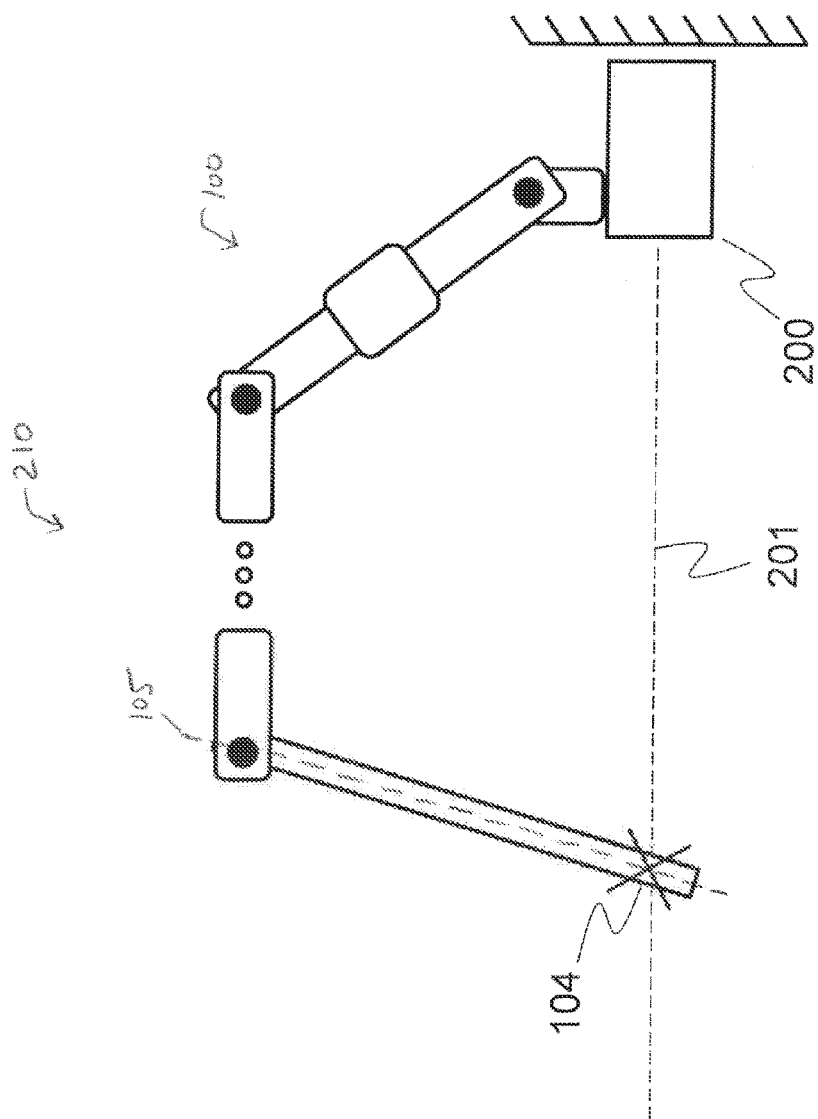
FIG. 3 illustrates a planar remote center of motion device attached to a rotational device, according to an embodiment of the invention.

FIG. 3 illustrates the planar remote center of motion device 100 attached to a rotational device 200, according to an embodiment of the invention. In order to achieve a remote center of motion assembly 210 capable of microsurgical procedures, the planar remote center of motion device 100 is mounted to a rotational device 200 such that the axis of rotation 201 of the rotational device 200 substantially passes through the remote center of motion 104 of the planar remote center of motion device 100. The rotational device 200 can rotate the planar remote center of motion device 100, and hence the surgical instrument 101, about the axis of rotation 201. In the configuration of FIG. 3, the planar region corresponding to the planar remote center of motion device 100 is therefore defined based on a rotational orientation of the planar remote center of motion device 100 defined about the axis of rotation 201.

Referring to FIGS. 2 and 3, the remote center of motion 104 is at a location on the axis 105 of the surgical instrument 101, such that motion of the surgical instrument 101 is subject to this location remaining stationary with respect to the patient, with the exception of motion along an axis 105 of the surgical instrument 101. For example, this location remains stationary with respect to the patient when the surgical instrument 101 is rotated about an axis passing through the remote center of motion 104. The location of the remote center of motion 104 may be at a penetration site of the patient, or may be elsewhere, depending on the type of surgery. For example, the remote center of motion 104 may be enforced for internal microsurgery, and may be disengaged for external microsurgery. In one embodiment, the surgical instrument 101 may have a single translational degree of freedom along the axis 105. For example, motion of the surgical instrument 101 along a first direction of the axis 105 may be to penetrate the patient, and motion along a second direction of the axis 105 opposite to the first direction may be to withdraw from the penetration site. The surgical instrument 101 may also have up to three rotational degrees of freedom. For example, the planar remote center of motion device 100, and hence the surgical instrument 101, may be rotated about the axis of rotation 201. The planar remote center of motion device 100 may also rotate the surgical device 101 about an axis substantially perpendicular to the planar region, and about the axis 105 passing through the surgical instrument 101.

The precision of enforcement of the remote center of motion 104 should fit the surgical need. For example, for internal microsurgery the remote center of motion 104 can be enforced with sub-millimeter precision. Precise control of the remote center of motion 104, by reducing unnecessary motion of the surgical instrument 101 at the penetration site of the patient, can reduce damage to patient tissue resulting from surgery.

In one embodiment, there may be a separate remote center of motion for each surgical instrument 101, and these multiple remote centers of motion can be enforced simultaneously. The remote center of motion 104 can be modified during surgery, or can remain stationary throughout surgery. The remote center of motion 104 may be controlled mechanically, such as by control of the motion of the planar remote center of motion device 100, and/or by software executing on the computer 114 (further described with reference to FIG. 12).

To perform microsurgery, two of the remote center of motion assemblies 210 are typically used. In microsurgery, the tissue being operated on, e.g., the eye during ocular microsurgery, is typically small. As a result, the remote centers of motion 104 of the two remote center of motion assemblies should be spatially separate and in close proximity for microsurgery. In one embodiment, the remote centers of motion 104 of the two remote center of motion assemblies 210 should be separated by no more than 2 centimeters, such as in the range from about 0.5 centimeters to about 2 centimeters, from about 1 centimeter to about 2 centimeters, and from about 1.5 centimeters to 2 centimeters. A microsurgical assembly 120 (see FIG. 1) including two remote center of motion assemblies 210 having remote centers of motion 104 in close proximity would facilitate telemicrosurgery, telementoring, cooperative surgery, and automated intraocular microsurgical procedures.

Figure 4:
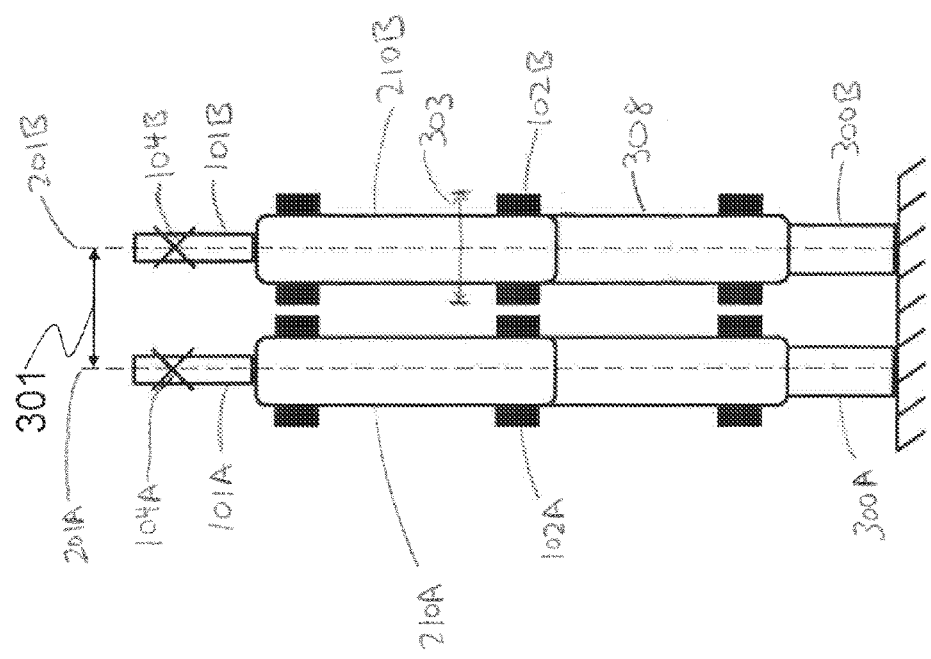
FIG. 4 illustrates a top view of a first remote center of motion assembly positioned adjacent to a second remote center of motion assembly, according to an embodiment of the invention.

FIG. 4 illustrates a top view of a first remote center of motion assembly 210A positioned adjacent to a second remote center of motion assembly 210B, according to an embodiment of the invention. The first remote center of motion assembly 210A has a first remote center of motion 104A on an axis of rotation 201A, and the second remote center of motion assembly 210B has a second remote center of motion 104B on an axis of rotation 201B. The first remote center of motion 104A and the second remote center of motion 104B are separated by a distance 301. In FIG. 4, the two remote center of motion assemblies 210A and 210B are aligned such that rotational joints 102A and 102B and rotational joints 300A and 300B of the assemblies 210A and 210B, respectively, are aligned in parallel. This alignment of the two remote center of motion assemblies 210A and 210B is advantageous in that the range of motion of surgical instruments 101A and 101B remains large, while collision avoidance between the two assemblies 210A and 210B is essentially reduced to comparing a first angle about the axis of rotation 201A and a second angle about the axis of rotation 201B (further described with reference to FIG. 7). Also, in FIG. 4, the two remote center of motion assemblies 210A and 210B are configured substantially symmetrically relative to the axes 201A and 201B, respectively. In one embodiment, the distance 301 can have a minimum value equal to a diameter 303 of the remote center of motion assembly 210. The diameter 303 spans a body 308 of the remote center of motion assembly 210, and the rotational joint 102. Due to the bulkiness of a typical remote center of motion assembly 210, the minimum value of the distance 301 may still be larger than the desired spacing of the remote centers of motion 104 for microsurgery.

Given that it is desirable to position the remote centers of motion 104A and 104B in close proximity, it may be advantageous to offset portions of the remote center of motion assemblies 210 from the axes of rotation 201A and 201B, respectively, so that the distance between the remote centers of motion 104A and 104B can be smaller than the largest diameter 303 of the remote center of motion assembly 210. FIG. 5 illustrates a top view of a first remote center of motion assembly 310A positioned adjacent to a second remote center of motion assembly 310B, where the two assemblies 310 are in an offset configuration, according to an embodiment of the invention. In one embodiment, a portion 312A of the first remote center of motion assembly 310A is offset from the axis of rotation 201A, and a portion 312B of the second remote center of motion assembly 310B is offset from the axis of rotation 201B. The portions 312A and 312B may be offset from the axes 201A and 201B, respectively, in opposite directions. By offsetting the portions 312A and 312B, a distance 305 between the remote centers of motion 104A and 104B can be reduced from the diameter 303, and therefore can be smaller than the distance 301. For example, in the configuration of FIG. 5, the distance 305 can have a minimum value equal to a diameter 313 of rotational joint 320. As a result, the configuration of FIG. 5 allows for a minimum value of the distance 305 that is less than 2 centimeters, and is therefore within the range of desired spacing of the remote centers of motion 104 for microsurgery.

Figure 6A:
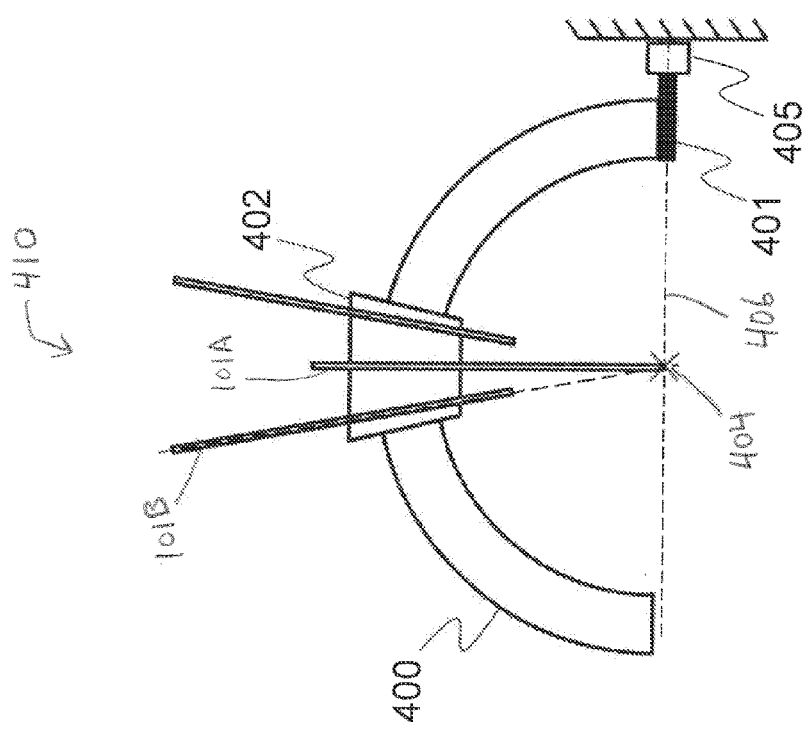
FIG. 6A through FIG. 6B illustrate a remote center of motion assembly including a carriage mounted to a substantially semi-circular track, where the carriage holds multiple surgical instruments, according to an embodiment of the invention.
Figure 6B:
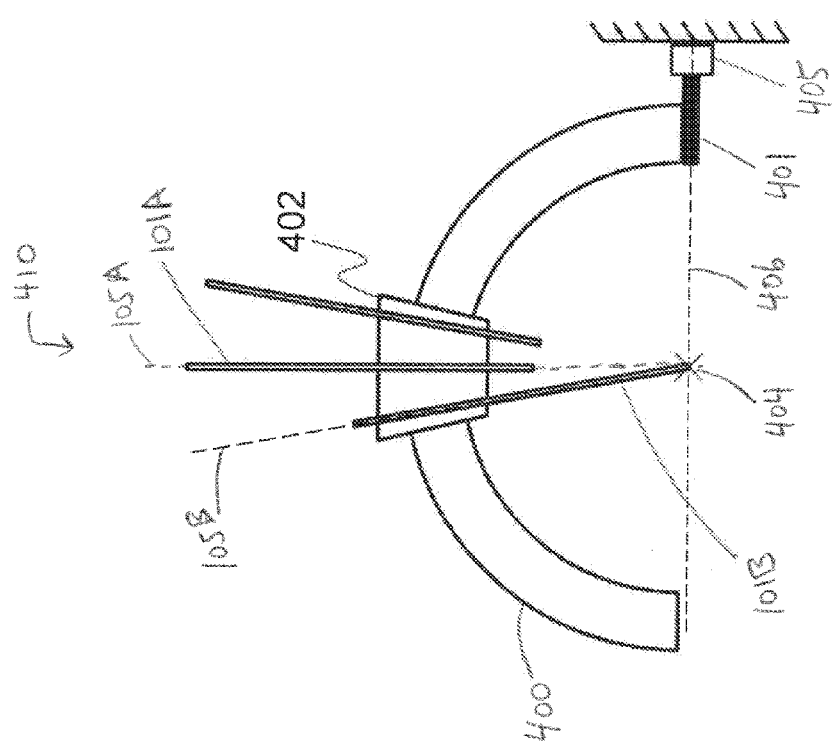

FIG. 6A through FIG. 6B illustrate a remote center of motion assembly 410 including a carriage 402 mounted to a substantially semi-circular track 400, where the carriage 402 holds multiple surgical instruments 101, according to an embodiment of the invention. Alternatively, the carriage 402 may hold a single surgical instrument 101. The remote center of motion assembly has a remote center of motion 404 substantially located at a center of the substantially semi-circular track 400. The positioning of the remote center of motion 400 at the center of the substantially semi-circular track 400 simplifies enforcement of the remote center of motion 404 as described with references to FIGS. 2 and 3. The carriage 402 may be a prismatic joint. The semicircular track 400 is attached to a small diameter shaft 401 pressed into a bearing 405. Referring to FIG. 6A, a surgical instrument 101A is attached to the carriage 402 such that it passes through a rotational axis 406 of the shaft 401 and the remote center of motion 404. Referring to FIG. 6B, the surgical instrument 101A is withdrawn from the remote center of motion 404 (relative to the configuration of FIG. 6A) through translation along its axis 105A. The surgical instrument 101B passes through the rotational axis 406 and the remote center of motion 404, having been translated along its axis 105B relative to the configuration of FIG. 6A.

In one embodiment, the remote center of motion assembly 410 provides one translational and three rotational degrees of freedom for the surgical instruments 101, similar to the remote center of motion assembly 210 of FIG. 3. In addition to translation along the axes 105 and rotation about the axis 406, the surgical instruments 101 can be rotated about the axes 105 through the surgical instruments 101. Through translation of the carriage 402 along the substantially semi-circular track 400, the surgical instruments 101 can also be rotated about an axis substantially perpendicular to a planar region defined by the axis 406 and the axes 105.

Figure 6C:
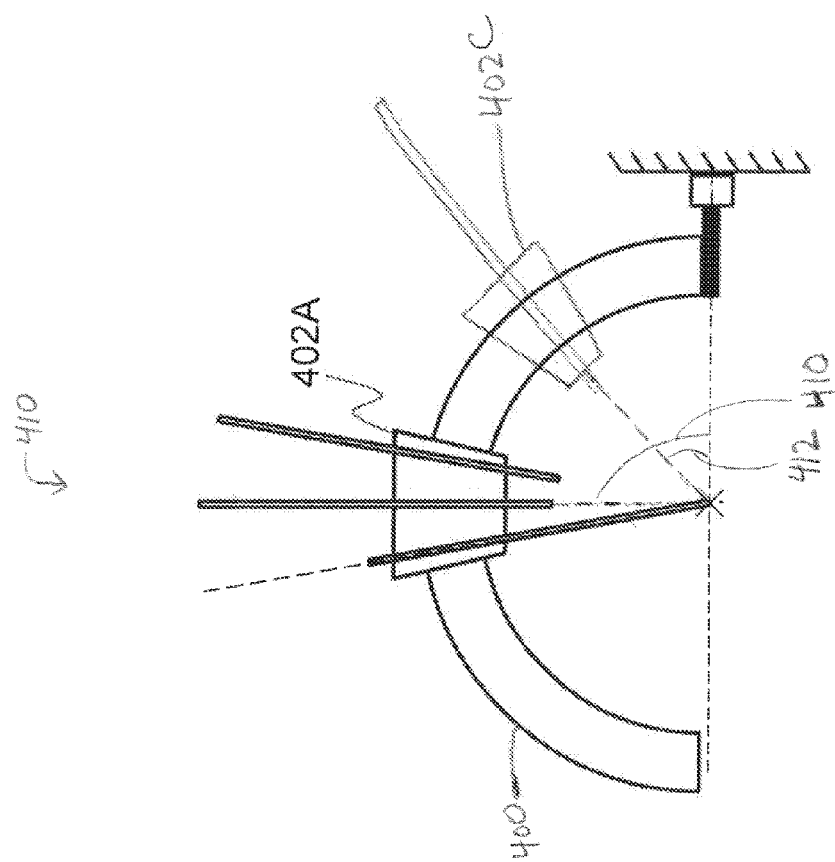
FIG. 6C illustrates a remote center of motion assembly including multiple carriages mounted to a substantially semi-circular track, according to an embodiment of the invention.

FIG. 6C illustrates the remote center of motion assembly 410 including multiple carriages 402A and 402C mounted to the substantially semi-circular track 400, according to an embodiment of the invention. The positioning of the carriages 402A and 402C on the substantially semi-circular track 400 simplifies maintenance of spatial separation, e.g. prevention of collisions, between the carriages 402A and 402C. A position of the carriage 402A on the track 400 may be defined by a first angle 410, and a position of the carriage 402C on the track 400 may be defined by a second angle 412. In one embodiment, a controller (not shown) may control the first angle 410 and the second angle 412 to maintain spatial separation between the carriages 402A and 402C. The controller may maintain spatial separation between the carriages 402A and 402C by comparing the first angle 410 and the second angle 412, taking into account the angular width of the carriages 402A and 402C on the track 400. For example, the controller may control the first angle 410 and the second angle 412 such that the absolute value of the difference between the first angle 410 and the second angle 412 is greater than at least half the sum of the angular widths of the carriages 402A and 402C on the track 400. Alternatively, software executing on the computer 114 may perform this control.

In one embodiment, multiple surgical instruments 101 may be attached to each carriage 402 in order to facilitate a complete surgical procedure without any manual intervention to change instruments. As shown in FIG. 6, the surgical instruments 101 are attached to the carriage 402 such that when moved axially they pass through the remote center of motion 404. The carriage 402 may include a universal cartridge allowing the use of any instrument, whether disposable or reusable. The carriage 402 may have one standard interface, capable of holding the cartridge and supplying utilities common to surgical instruments, e.g., vacuum, video, light, laser, etc. Each cartridge is made to hold the required surgical instrument on one side and to fit the standard interface on the other side.

In one embodiment, the surgical instruments 101 are held in a magazine that allows the appropriate instrument to be staged for an instrument change. During an instrument change, an instrument may be removed from the carriage 402 and may be replaced by an instrument from the magazine. Also, the instrument from the magazine may then be replaced by the instrument from the carriage 402. This may be done in a sterile environment, and may be automated.

Figure 7:
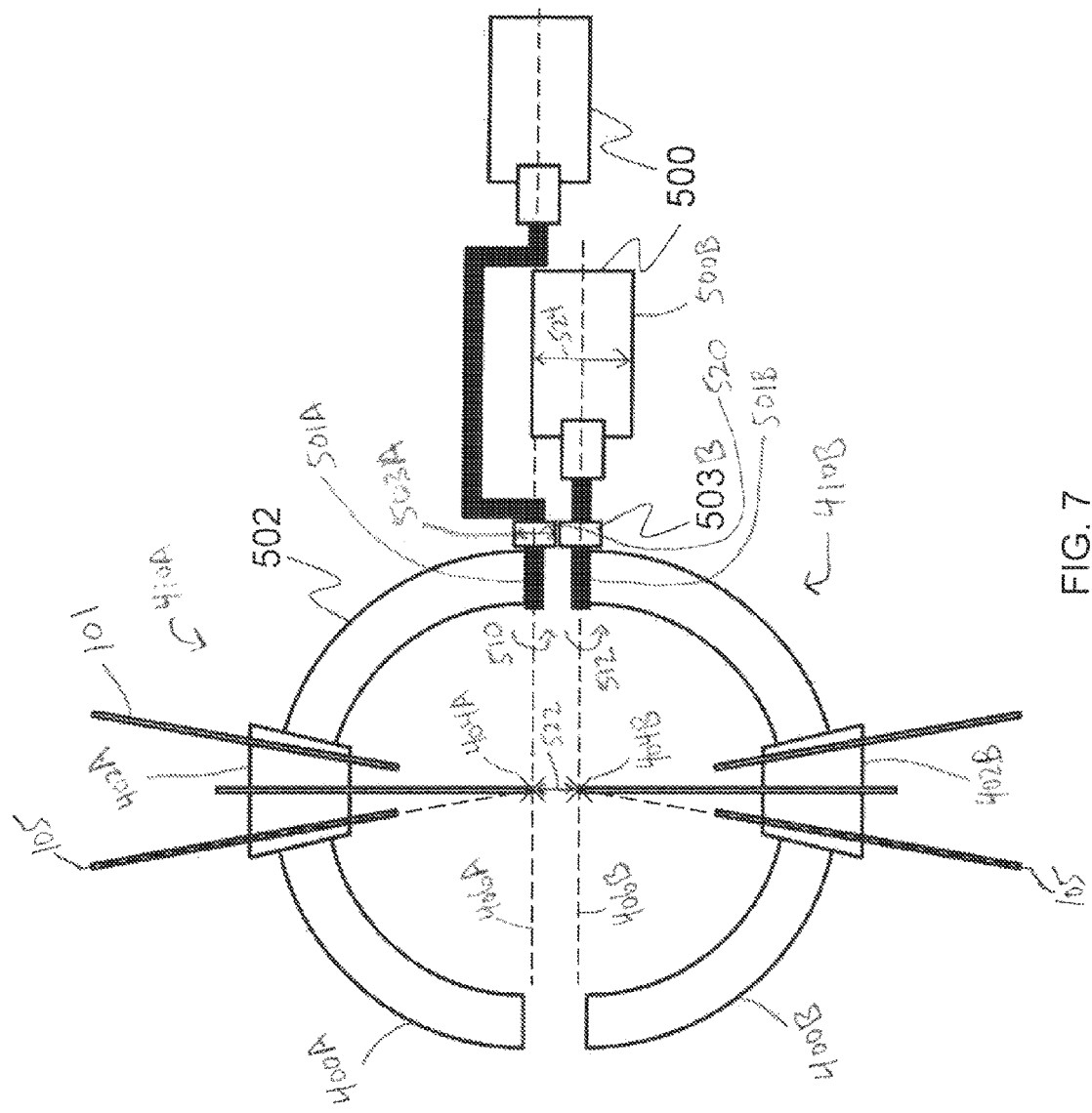
FIG. 7 illustrates a first remote center of motion assembly positioned adjacent to a second remote center of motion assembly and oriented 180 degrees opposed to the second remote center of motion assembly, where each of the two assemblies include a carriage mounted to a substantially semi-circular track, according to an embodiment of the invention.

FIG. 7 illustrates a first remote center of motion assembly 410A positioned adjacent to a second remote center of motion assembly 410B and oriented 180 degrees opposed to the second remote center of motion assembly 410B, where each of the two assemblies 410 include the carriages 402A and 402B mounted to substantially semi-circular tracks 400A and 400B, according to an embodiment of the invention. Similar to FIGS. 6A through 6C, the tracks 400A and 400B are attached to small diameter shafts 501A and 501B pressed into bearings 503A and 503B, respectively, and connected to motors 500. The tracks 400A and 400B can be rotated about the axes of rotation 406A and 406B, which pass through the shafts 501A and 501B, respectively. To place to remote centers of motion 404A and 404B within close proximity of each other, the two symmetrically opposite assemblies 410A and 410B may be placed next to each other such that the axes of rotation 406A and 406B of the shafts 501A and 501B are parallel. Similar to the previous discussion with reference to FIG. 5, a portion of the shaft 501A is offset from the axis of rotation 406A to clear the motor 500B, so that a distance 522 between the remote centers of motion 404A and 404B can be smaller than a diameter 524 of the motors 500. The offset may be in the direction from the axis of rotation 406B to the axis of rotation 406A. Because of the offset, the closest that the remote centers of motion 404A and 404B can be is a diameter 520 of the bearings 503, which is typically smaller than the diameter 524.

In one embodiment, the shafts 501A and 501B may be driven by crankshafts. The crankshafts may extend from the motors 500 to the bearings 503. This may be advantageous because there is little or no added slip or backlash. Alternatively, the shafts 501A and 501B may be driven by belts, friction drives, or gears.

In one embodiment, passive dampers or active actuators can be attached to the shafts 501. In teleoperated microsurgical applications, actuators are used. During cooperative surgical instrument manipulation, actuators or passive dampers can be used to reduce surgical tremor.

Figure 8:
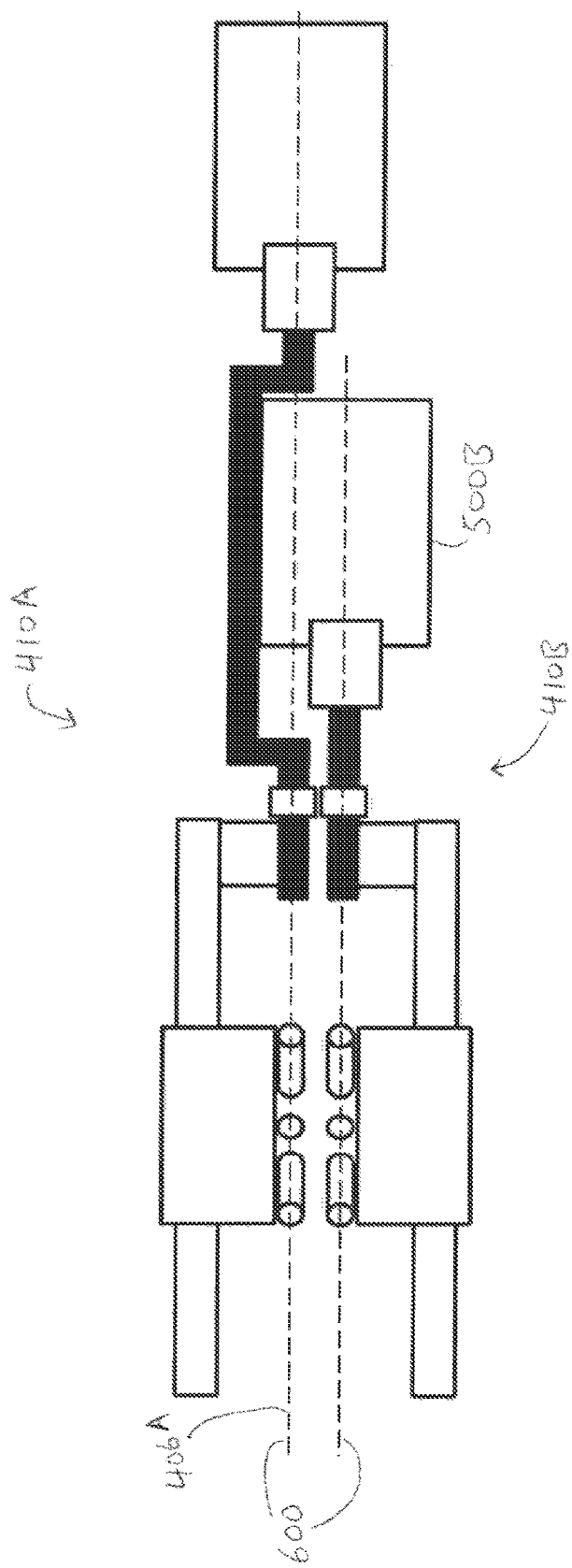
FIG. 8 illustrates a top view of the first remote center of motion assembly of FIG. 7 positioned adjacent to the second remote center of motion assembly of FIG. 7 and oriented substantially parallel to the second remote center of motion assembly, according to an embodiment of the invention.

FIG. 8 illustrates a top view of the first remote center of motion assembly 410A of FIG. 7 positioned adjacent to the second remote center of motion assembly 410B of FIG. 7 and oriented substantially parallel to the second remote center of motion assembly 410B, according to an embodiment of the invention. Referring to FIG. 8, in one embodiment the motor 500B of the remote center of motion assembly 410B may cross the axis of rotation 406A of the remote center of motion assembly 410A.

The configuration of FIG. 7 allows for a large range of motion needed during many microsurgical procedures. The surgical instruments 101 can be oriented such that their centerlines 105 lie in a single plane 502. In this configuration, the absolute value of the difference between the first angle 510 about the axis of rotation 406A and the second angle 512 about the axis of rotation 406B is 180 degrees. Referring to FIG. 8, the surgical instruments 101 may also be configured such that they lie in parallel planes 600 which are separated by the diameter 520 of the bearings 503. In this configuration, the absolute value of the difference between the first angle 510 about the axis of rotation 406A and the second angle 512 about the axis of rotation 406B may be 0 degrees.

Referring to FIGS. 7 and 8, in one embodiment, a controller (not shown) may control the first angle 510 and the second angle 512 to maintain spatial separation between the carriages 402A and 402B. The controller may maintain spatial separation between the carriages 402A and 402B by comparing the first angle 510 and the second angle 512. In one embodiment, the distance 522 between the remote centers of motion may be configured such that in the configuration of FIG. 8, the carriages 402A and 402B are barely in physical contact. For example, the controller may control the first angle 510 and the second angle 512 such that the first angle 510 is less than the second angle 512. Alternatively, depending on the reference from which the first angle 510 and the second angle 512 are measured, the controller may control the first angle 510 and the second angle 512 such that the first angle 510 is greater than the second angle 512. Alternatively, software executing on the computer 114 may perform this control.

In the configuration of FIGS. 7 and 8, through translation of the carriages 402 along the substantially semi-circular track 400, the surgical instruments 101 have a rotational range of motion of up to approximately 180 degrees about an axis substantially perpendicular to a planar region defined by the axes 406 and the axes 105. This range of motion may be reduced if there are multiple carriages 402 disposed on the same track 400, and may be further reduced by the positioning of human tissue during surgery. The surgical instruments 101 have a rotational range of motion about the axes 406 and the axes 105 of up to 360 degrees. These range of motion may be reduced by the positioning of human tissue during surgery. The ranges of motion made possible by the configuration of FIGS. 7 and 8 is sufficient for microsurgical applications, for which a rotational range of motion of at least 150 degrees may be desirable.

Figure 9:
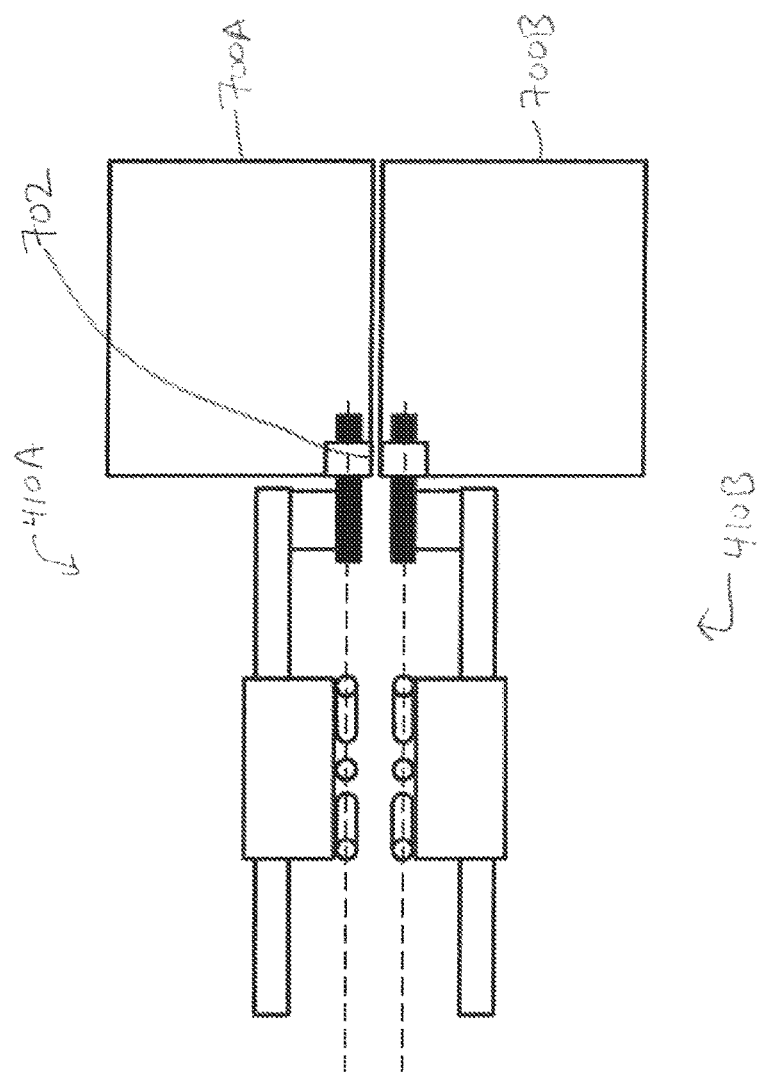
FIG. 9 illustrates a top view of a first remote center of motion assembly and a second remote center of motion assembly, where each of the two assemblies is mounted to an XYZ stage, according to an embodiment of the invention.

FIG. 9 illustrates a top view of the first remote center of motion assembly 410A and the second remote center of motion assembly 410B, where each of the two assemblies 410 is mounted to an XYZ stage 700, according to an embodiment of the invention. During surgery it may be desirable to move the remote center of motion. This involves moving the assemblies 410A and 410B with respect to the patient. This can be accomplished by mounting each of the assemblies 410A and 410B to its corresponding XYZ stage 700A and 700B, respectively. To prevent each XYZ stage 700 from colliding with the opposing assembly or stage, each XYZ stage 700 can be mounted such that, for example, the XYZ stage 700A is behind the assembly 410A and flush with the bearing surface 702 facing the opposing assembly 410B.

Figure 10A:
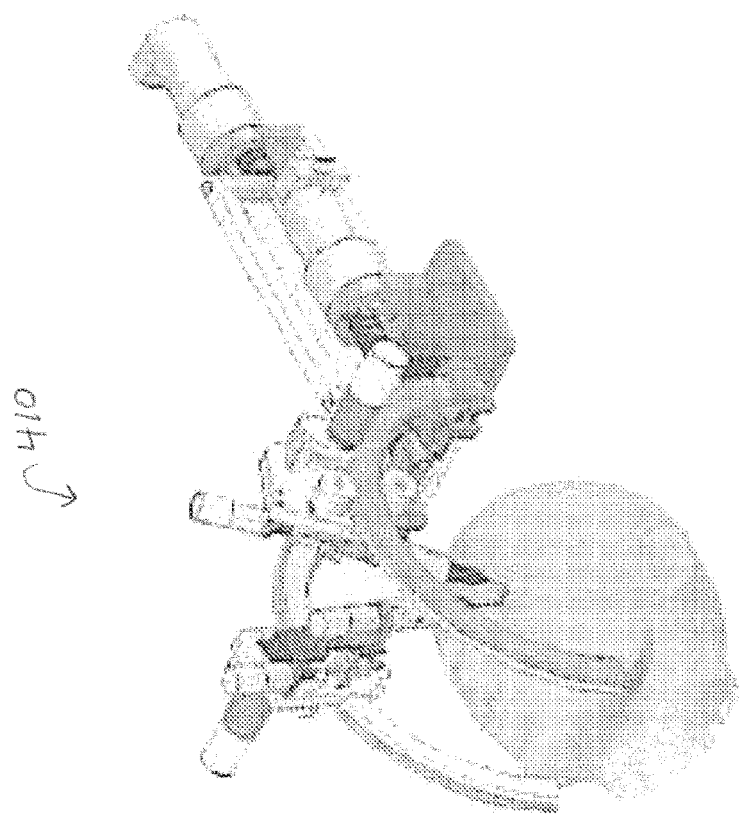
FIG. 10A through FIG. 10C illustrate perspective views of the first remote center of motion assembly of FIG. 7 positioned adjacent to the second remote center of motion assembly of FIG. 7, according to an embodiment of the invention.
Figure 10B:
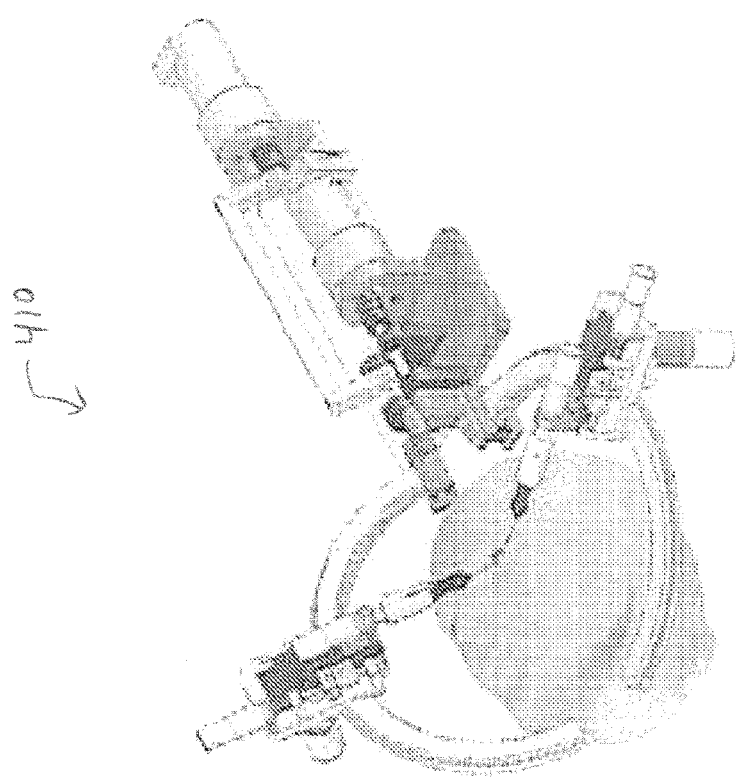
Figure 10C:
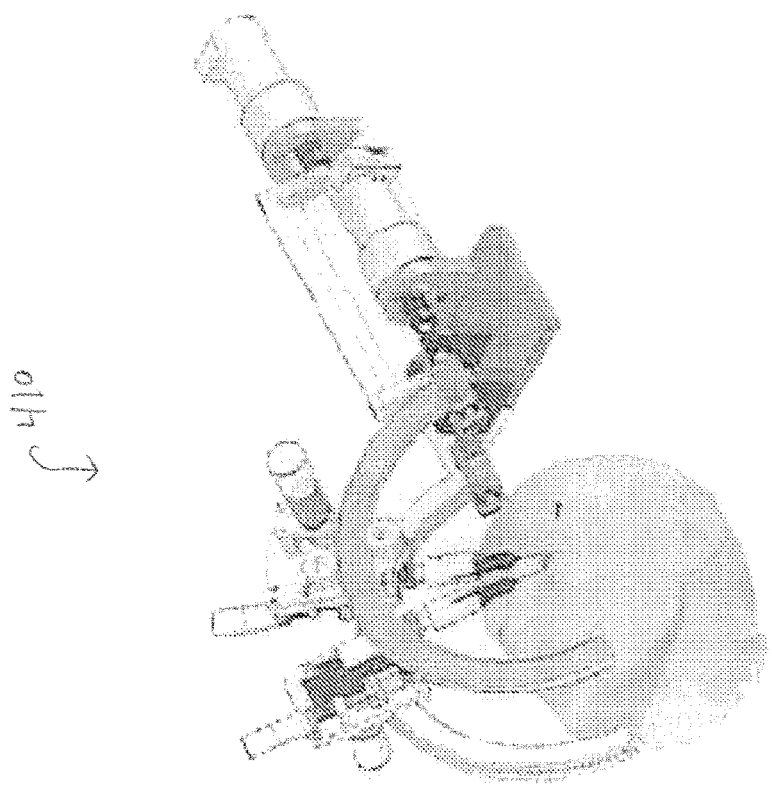

FIG. 10A through FIG. 10C illustrate perspective views of the first remote center of motion assembly 410A of FIG. 7 positioned adjacent to the second remote center of motion assembly 410B of FIG. 7, according to an embodiment of the invention. These views show examples of the range of rotational motion of the remote center of motion assemblies 410.

Figure 11:
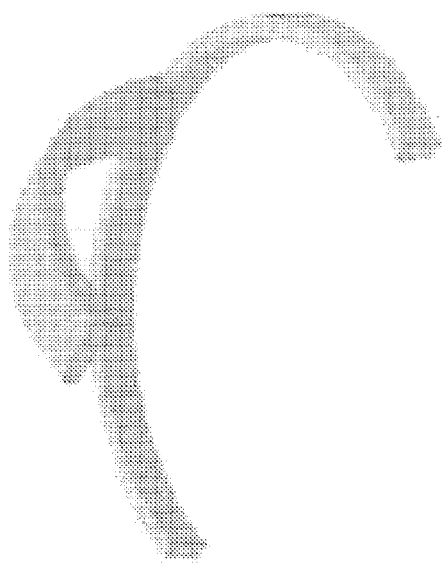
FIG. 11 illustrates a head restraint for use in the system for robotic microsurgery, according to an embodiment of the invention.

FIG. 11 illustrates a head restraint 1100 for use in the system 110 for robotic microsurgery, according to an embodiment of the invention. The head restraint 1100 may be configured to be attached to a patient so that motion of the head restraint 1100 corresponds to motion of the head of the patient. In one embodiment, a controller may be configured to move the remote center of motion assemblies 410 (see FIG. 7) based on the motion of the restraint 1100, such that the remote centers of motion 404 (see FIG. 7) move corresponding to the motion of the patient. The controller may damp and/or otherwise perform filtering to control the motion of the remote centers of motion 404 in response to the motion of the restraint 1100. In one embodiment, if motion of the patient detected by the restraint 1100 exceeds a threshold, the controller may abort the surgery. Alternatively, software executing on the computer 114 may perform this control.

Figure 12:
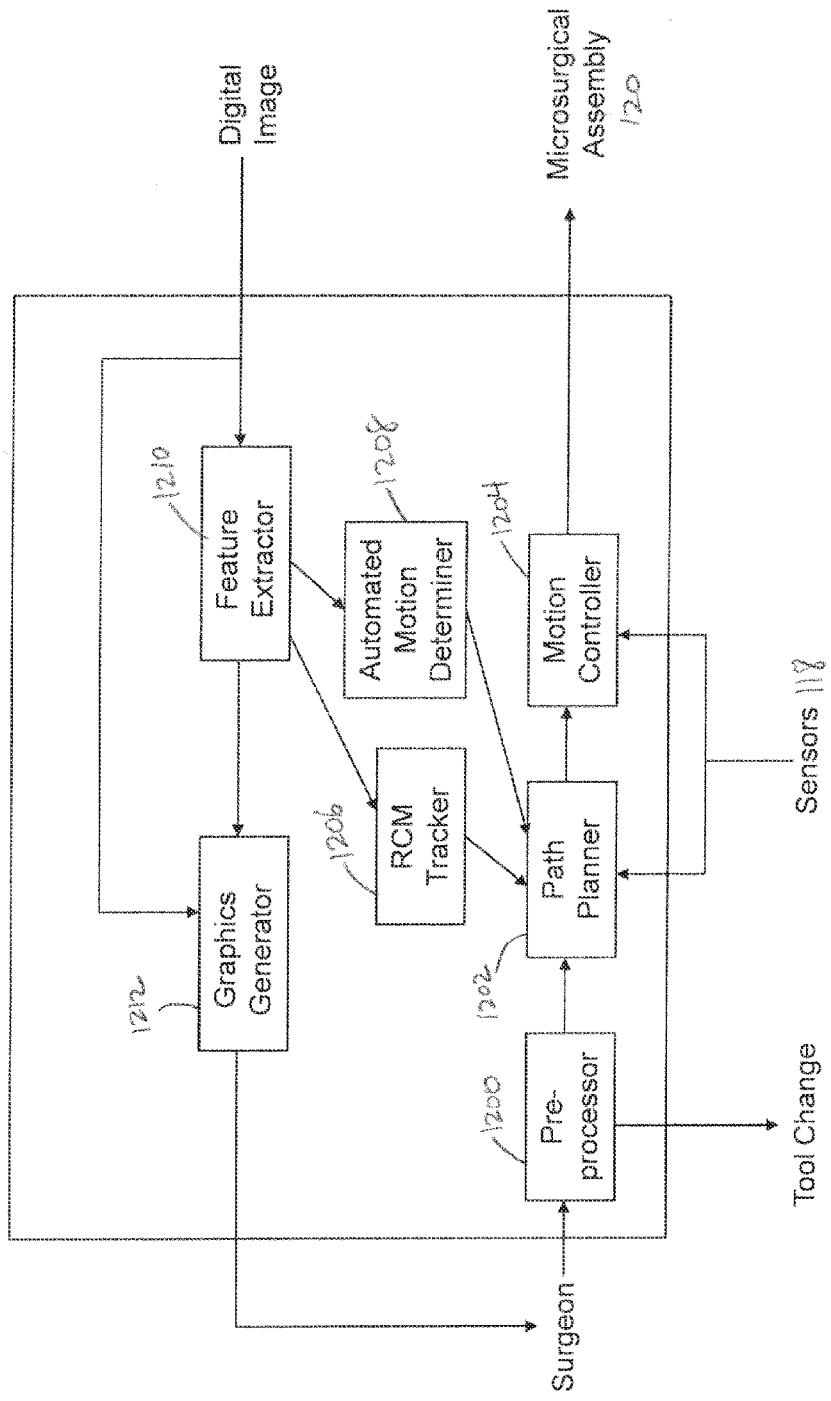
FIG. 12 illustrates a computer included in a system for robotic microsurgery, according to an embodiment of the invention.

FIG. 12 illustrates the computer 114 included in the system 110 for robotic microsurgery, according to an embodiment of the invention. As described previously with reference to FIG. 1, the computer 114 receives inputs from the controls 112 manipulated by the surgeon. A pre-processor module 1200 processes the inputs from the controls 112. A result of this processing may be a determination that a surgical instrument change has been requested (described previously with reference to FIG. 6). In addition, the pre-processor module 1200 may determine that the surgeon has requested translation and/or rotation motion of a surgical instrument, and may provide this input to a path planner module 1202. The path planner module 1202 may also receive input from the sensors 118. For example, sensors associated with the head restraint 1100 (see FIG. 11) may report motion of the patient's head. The path planner module 1202 may also receive input from a remote center of motion tracker module 1206 and an automated motion determiner module 1208. The path planner module 1202 takes these various inputs into account when determining what input to provide to the motion controller module 1204.

In one embodiment, the remote center of motion tracker module 1206 may estimate motion of the remote center of motion due to, for example, patient motion. This estimation may be based on features extracted by a feature extractor module 1210. The feature extractor module 1210 may extract features from digital images based on image processing and/or machine vision algorithms known to one of ordinary skill in the art. In one embodiment, the automated motion determiner module 1208 may control automatic motion of one or more robotic arms of the microsurgical assembly 120. For example, the automated motion determiner module 1208 may track the site of a surgical procedure with an endoscope using a robotic arm of the microsurgical assembly 120. This tracking may be based on features extracted by the feature extractor module 1210. In this example, the feature extractor module 1210 may extract features from digital images provided by the endoscope.

In one embodiment, the graphics generator module 1212 may generate images for viewing by the surgeon. For example, the generated images may be composite images highlighting areas of interest detected by the feature extractor module 1210. These generated images may provide the surgeon with an enhanced view of the surgical field.

In one embodiment, the path planner module 1202 requests motion of the microsurgical assembly 120 based on the motion requests from the surgeon, the remote center of motion tracker module 1206, and the automated motion determiner module 1208. This reference trajectory provided by the path planner module 1202 is then tracked precisely by the motion controller 1204 using, for example, feedback control algorithms known to one of ordinary skill in the art.

In one embodiment, the computer 114 includes standard components, such as input/output interfaces, a central processing unit, and memory. The memory includes executable instructions establishing the various modules described with reference to FIG. 12. The modules shown in FIG. 12 are exemplary. The function of individual modules may be combined. In addition, the modules may be distributed across a network.

An embodiment of the invention relates to a computer storage product with a computer-readable medium having computer code thereon for performing various computer-implemented operations. The term "computer-readable medium" is used herein to include any medium that is capable of storing or encoding a sequence of instructions or computer codes for performing the operations described herein. The media and computer code may be those specially designed and constructed for the purposes of the invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily be drawn to scale, and manufacturing tolerances may result in departure from the artistic renditions herein. There may be other embodiments of the present invention which are not specifically illustrated. Thus, the specification and the drawings are to be regarded as illustrative rather than restrictive. Additionally, the drawings illustrating the embodiments of the present invention may focus on certain major characteristic features for clarity. Furthermore, modifications may be made to adapt a particular situation, material, composition of matter, method, or process to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A system for microsurgery comprising:
a first assembly and a second assembly, each including:
   a planar remote center of motion device configured to constrain motion of a surgical instrument attached to the planar remote center of motion device such that an axis of the surgical instrument passes through a remote center of motion while remaining in a planar region defined based on a rotational orientation of the planar remote center of motion device; and
   a rotational device attached to the planar remote center of motion device and configured such that an axis of rotation of the rotational device passes through the remote center of motion, wherein the rotational orientation of the planar remote center of motion device is defined about the axis of rotation;
wherein the first assembly and the second assembly are configured to be positioned such that the remote center of motion of the first assembly and the remote center of motion of the second assembly are maintained spatially separate, and a distance between the remote center of motion of the first assembly and the remote center of motion of the second assembly is no greater than two centimeters,
wherein the first assembly is configured to be positioned adjacent to the second assembly such that at least a portion of the rotational device of the first assembly is offset from the axis of rotation of the rotational device of the first assembly,
wherein:
   the rotational device of the second assembly includes a motor having a diameter greater than the distance between the remote center of motion of the first assembly and the remote center of motion of the second assembly; and the at least a portion of the rotational device of the first assembly includes a shaft, wherein the shaft is offset to accommodate the motor.

2. A method of controlling motion of surgical instruments, comprising:
  positioning a first device and a second device such that a first remote center of motion associated with the first device and a second remote center of motion associated with the second device are maintained as spatially separate and in close proximity for microsurgery;
  attaching a first surgical instrument to the first device, wherein the first device constrains motion of the first surgical instrument such that an axis of the first surgical instrument passes through the first remote center of motion;
  attaching a second surgical instrument to the second device, wherein the second device constrains motion of the second surgical instrument such that an axis of the second surgical instrument passes through the second remote center of motion; and
  rotating the first device and the second device, while maintaining spatial separation between the first device and the second device and between the first surgical instrument and the second surgical instrument based on a first rotational orientation of the first device and a second rotational orientation of the second device, wherein:
  the first device includes a first portion having a diameter greater than a distance between the first remote center of motion and the second remote center of motion; and
  the second device includes a second portion that is offset to clear the first portion of the first device.

3. The method of claim 2, wherein:
  the first rotational orientation is defined by a first angle about a first axis of rotation;
  the second rotational orientation is defined by a second angle about a second axis of rotation; and
  maintaining spatial separation between the first device and the second device and between the first surgical instrument and the second surgical instrument includes controlling the rotational orientation of the first device and the rotational orientation of the second device such that the first angle is less than the second angle.

4. The method of claim 2, wherein:
  the first device includes a first carriage and a second carriage mounted to a substantially semi-circular track;
  at least one of the first carriage and the second carriage is configured to be attached to the first surgical instrument;
  a first position of the first carriage on the substantially semi-circular track is defined by a first angle;
  a second position of the second carriage on the substantially semi-circular track is defined by a second angle; and
  positioning the first device includes maintaining spatial separation between the first carriage and the second carriage by controlling the first angle and the second angle.

5. A method of controlling motion of surgical instruments, comprising:
  positioning a first device and a second device such that a first remote center of motion associated with the first device and a second remote center of motion associated with the second device are maintained as spatially separate and in close proximity for microsurgery;
  attaching a first surgical instrument to the first device, wherein the first device constrains motion of the first surgical instrument such that an axis of the first surgical instrument passes through the first remote center of motion;
  attaching a second surgical instrument to the second device, wherein the second device constrains motion of the second surgical instrument such that an axis of the second surgical instrument passes through the second remote center of motion; and
  rotating the first device and the second device, while maintaining spatial separation between the first device and the second device and between the first surgical instrument and the second surgical instrument based on a first rotational orientation of the first device and a second rotational orientation of the second device, wherein positioning the first device and the second device includes maintaining a distance of no greater than two centimeters between the first remote center of motion associated with the first device and the second remote center of motion associated with the second device.

6. The method of claim 5, wherein:
  the first rotational orientation is defined by a first angle about a first axis of rotation;
  the second rotational orientation is defined by a second angle about a second axis of rotation; and
  maintaining spatial separation between the first device and the second device and between the first surgical instrument and the second surgical instrument includes controlling the rotational orientation of the first device and the rotational orientation of the second device such that the first angle is less than the second angle.

7. The method of claim 5, wherein:
  the first device includes a first carriage and a second carriage mounted to a substantially semi-circular track;
  at least one of the first carriage and the second carriage is configured to be attached to the first surgical instrument;
  a first position of the first carriage on the substantially semi-circular track is defined by a first angle;
  a second position of the second carriage on the substantially semi-circular track is defined by a second angle; and
  positioning the first device includes maintaining spatial separation between the first carriage and the second carriage by controlling the first angle and the second angle.

* * * * *